(12) United States Patent
Armour

(10) Patent No.: US 7,484,848 B2
(45) Date of Patent: Feb. 3, 2009

(54) LENS-FREE OPHTALMOSCOPE

(76) Inventor: Roger Hanif Armour, 88 Wymondley Road, Hitchin, Hertfordshire SG4 9PX (GB)

(*) Notice: Subject to any disclaimer, the term of this patent is extended or adjusted under 35 U.S.C. 154(b) by 320 days.

(21) Appl. No.: 10/511,081

(22) PCT Filed: Dec. 18, 2002

(86) PCT No.: PCT/GB02/05758
§ 371 (c)(1),
(2), (4) Date: Oct. 12, 2004

(87) PCT Pub. No.: WO03/088828
PCT Pub. Date: Oct. 30, 2003

(65) Prior Publication Data
US 2005/0179864 A1 Aug. 18, 2005

(30) Foreign Application Priority Data
Apr. 17, 2002 (GB) .................................. 0208776.5

(51) Int. Cl.
*A61B 3/10* (2006.01)
(52) U.S. Cl. ........................................ 351/205
(58) Field of Classification Search ............... 351/205, 351/218, 221, 220
See application file for complete search history.

(56) References Cited

U.S. PATENT DOCUMENTS

| 5,880,713 A | * | 3/1999 | Belardinelli | 345/156 |
| 6,783,239 B2 | * | 8/2004 | Epitropoulos | 351/221 |
| 2004/0012759 A1 | * | 1/2004 | Lo | 351/205 |

FOREIGN PATENT DOCUMENTS

GB 2204144 A * 2/1988

* cited by examiner

*Primary Examiner*—Hung X Dang
*Assistant Examiner*—Tuyen Q Tra
(74) *Attorney, Agent, or Firm*—Fildes & Outland, P.C.

(57) ABSTRACT

A lens-free ophthalmoscope (21, 41) comprising means (22, 42) defining a first light path (a), reflective means (23, 43) arranged to divert light from the first light path (a) along a second light path (b) extending through a first window (24, 44) and into a subject eye (29, 49), a second window (25, 45) through which a user can view a subject generally parallel to the second light path (b), and a baffle (23, 26; 43, 46) arranged between the first light path (a) and second window (25, 45) to prevent, or at least substantially reduce, any light exiting the ophthalmoscope through the second window (25, 45). Hence, any light which might otherwise pass through the second window (25) int the eye (30, 50) of an user, is eliminated or at least substantially reduced, thereby substantially reducing glace and enhancing the user's view of the subject eye (29, 49).

12 Claims, 5 Drawing Sheets

LENS-FREE OPHTALMOSCOPE

FIELD OF THE INVENTION

This invention relates to ophthalmoscopes and especially, but not exclusively, to ophthalmoscopes which are simple and inexpensive to manufacture.

BACKGROUND OF THE INVENTION

An ophthalmoscope is usually a complex optical instrument used for examining the retina of humans and animals. Generally, ophthalmoscopes have more than twenty lenses and from three to six lights and, as such, are intricate and costly to manufacture and buy.

Examples of such know types of ophthalmoscope are disclosed in GB-A-2235308, GB-A-2204144, WO-A-2000/30527 and DE-A-3714041.

Ophthalmoscopes are used routinely during the day-to-day work of doctors, optometrists, veterinary surgeons, health workers and trainees of the above.

However, due to the expensive nature of this instrument, only limited numbers are available for actual use and certainly there is no way that an ophthalmoscope can be provided for each, for example, doctor who needs to use one.

Due to the shortage of these instruments and their complexity, students and even non-specialised medical staff very often do not get a chance to learn how to use this instrument properly.

This situation is worse in less developed and third world countries where in some places there are no ophthalmoscopes available to local doctors or aid workers, because they are simply too expensive to buy or manufacture.

The problem of the restricted numbers of ophthalmoscopes in hospitals, opticians and veterinary surgeries, along with the associated lack of expertise in using the instrument, when available, is therefore potentially serious and any attempt to reduce the complexity of the instrument and the manufacturing costs, is sought.

"Manufacture and Use of Homemade Ophthalmoscopes: a 150$^{th}$ Anniversary Tribute to Helmholtz" a publication from BMJ, 23-30 Dec. 2000, Vol 321, p1557-1559, discloses a simple ophthalmoscope. This instrument, although much simpler and cheaper to produce than standard ophthalmoscopes, has a major problem in that the sight hole through which the retina is observed, causes glare in the observer's eye, thereby severely reducing the view.

Any method of producing cheaply a simple ophthalmoscope which eliminates, or at least substantially reduces, the problems commonly associated with the simple ophthalmoscope disclosed in the above mentioned paper, is therefore sought.

PRESENT INVENTION

Accordingly it is an object of the present invention to overcome, or at least substantially reduce the disadvantages associated with known types of ophthalmoscope, such as those discussed above.

Thus, the invention provides a lens-free ophthalmoscope comprising:
means defining a first light path;
reflective means arranged to divert light from the first light path along a second light path exiting the ophthalmoscope through a first window and into a subject eye;
a second window through which an user can view a subject eye along a path extending generally parallel to the second light path; and
a baffle which is arranged between the first light path and the second window to prevent, or at least substantially reduce, any light exiting the ophthalmoscope through the second window.

The ophthalmoscope may also comprise a light source, which can be incorporated with the other components of the apparatus as another component thereof, or may be arranged to receive a separate, detachable light source.

The first light path defining means may comprise a tube wherein, preferably, at least the outer surface of the tube is opaque and the inner surface may be non-reflective.

The reflective means may comprise a mirror, preferably semicircular, which is inclined at approximately 45° to the first light path and/or the second light path. Alternatively, the reflective means may comprise a prism.

The first window can be an aperture in, for example, a tube defining the first light path. Any such aperture is preferably circular. The second window may be in the otherwise closed end of the tube, for example, in a roof of the tube. Again, this second window is preferably circular.

The reflective means may be associated with the baffle which is preferably either a flange or a block. With a block, the reflective means is preferably mounted thereon.

The positioning and dimensions of the baffle ensure that little or no light reaches the second window and, as a consequence, no, or very little, glare through the second window is experienced by an observer.

Thus, it can be seen that the lens-free nature of an ophthalmoscope in accordance with the invention, as defined above, provides an inexpensive product which is simple to use and prevents, or at least reduces substantially, any glare due to the prevention or at least substantial reduction, of any undesirable light exiting the ophthalmoscope via its second window into the eye of an observer.

DETAILED DESCRIPTION OF THE DRAWINGS

Figure 1:
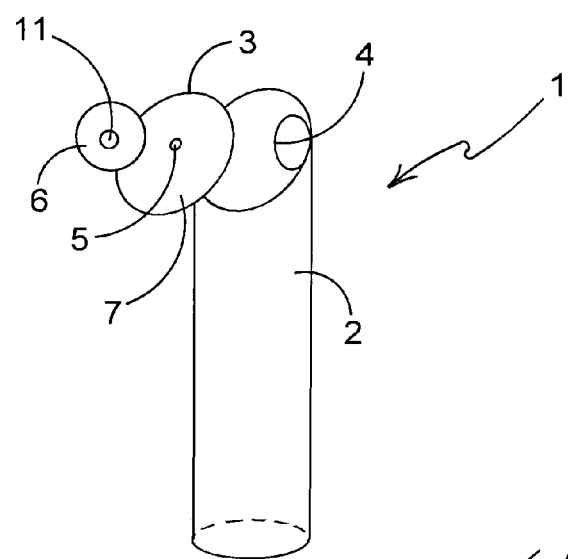
FIG. 1 shows a partial exploded view of a prior art ophthalmoscope.
Figure 2:
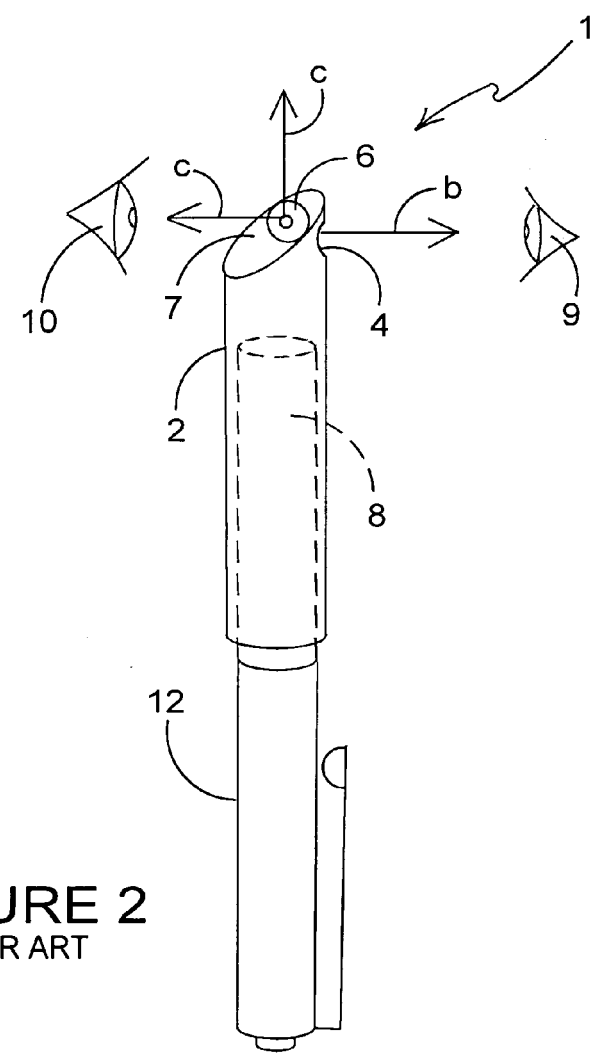
FIG. 2 shows the prior art ophthalmoscope of FIG. 1 assembled, with a detachable light source provided.
Figure 3:
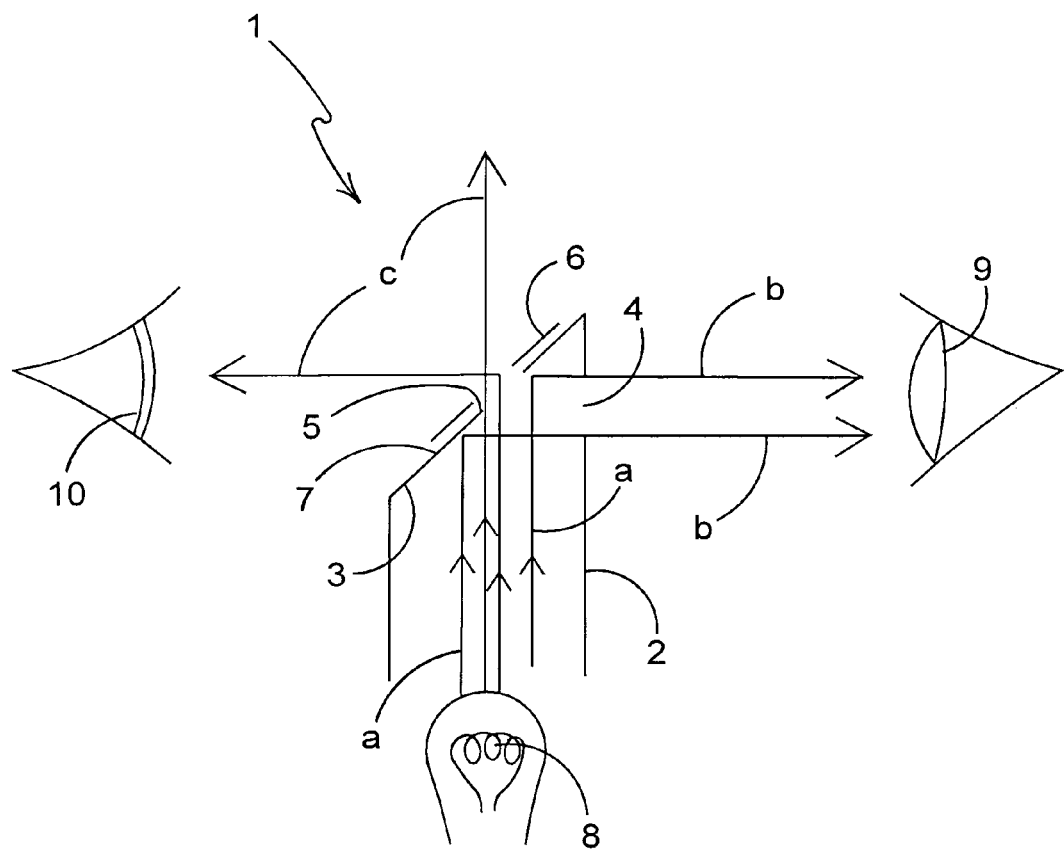
FIGS. 3 to 5 show the prior art ophthalmoscope of FIGS. 1 and 2 in use.
Figure 4:
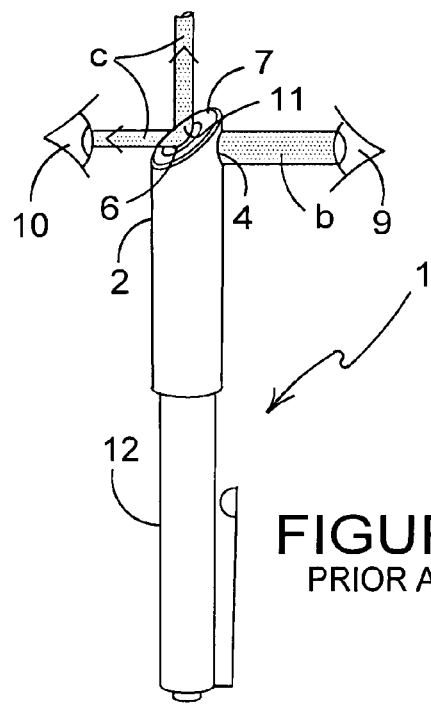
Figure 5:
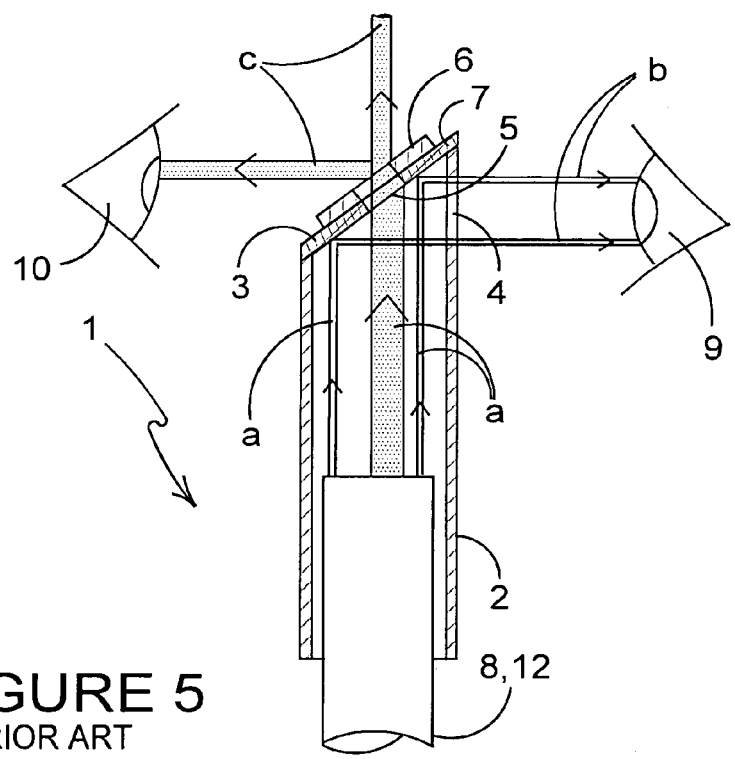

Referring firstly to FIGS. 1 to 5 of the drawings, a prior art lens-free ophthalmoscope, indicated generally at 1, comprises a tube 2 defining a first light path a, as shown in FIGS. 3 and 5, reflective means in the form of an oval mirror 3, a first window 4 in the form of a circular aperture in the side wall of the tube 2, a second window 5 in the form of a circular aperture in an oval roof 7 of the tube 2, and a glare disc 6, there being no lenses used.

The ophthalmoscope 1 is arranged such that the mirror 3 forms the underside of the inclined roof 7 of the tube 2, with the second window 5, passing generally centrally through the mirror 3.

This mirror 3 diverts light passing from a light source 8 along the first light path a, as shown in FIG. 3, along a second light path b exiting the tube 2 through the first window 4 and into a subject eye 9.

The second window 5 allows an user 10 to view the subject eye 9 along a path extending generally parallel to and coincident with the second light path b.

However, as can be seen from FIGS. 2, 3 and 5, this design has a problem, in that the second window 5 causes glare, as indicated diagrammatically at C, in the eye 10 of an observing user, thereby severely reducing the view of the subject eye 9, because some of the light from light path a exits through the second window 5, causing this undesirable glare at the eye 10 of the observer.

In order to reduce this glare, the glare disc 6 is secured to the upper surface of the inclined roof 7 of the tube 2, with a centrally-located, circular aperture 11 lying in-register with the circular aperture of the second window 5. In effect, the thickness of the glare disc 6 in the region of the central aperture 11 increases the total thickness of the two apertures 5 and 9, in an attempt to reduce glare at the eye 10 of the observer.

However, and as discussed briefly above, such a remedy was unsuccessful, with an observing user still experiencing an unreasonable amount of glare passing through the respective in-register apertures 5, 11 of the tube roof 7 and glare disc 6.

As can be seen from FIG. 2, the light source 8 is provided by a light pen 12 inserted in the bottom end of the tube 2 which is opaque and which preferably has a matt black, non-reflective inner surface.

In order to eliminate, or at least substantially reduce, this glare associated with the known ophthalmoscope 1 discussed above in relation to FIGS. 1 to 5, a lens-free ophthalmoscope in accordance with the invention is provided with a baffle arranged between the first light path and second window, as will be described in more detail hereinbelow with respect to the two embodiments of inventive ophthalmoscope shown in FIGS. 6 and 7 to 9 respectively.

Figure 6:
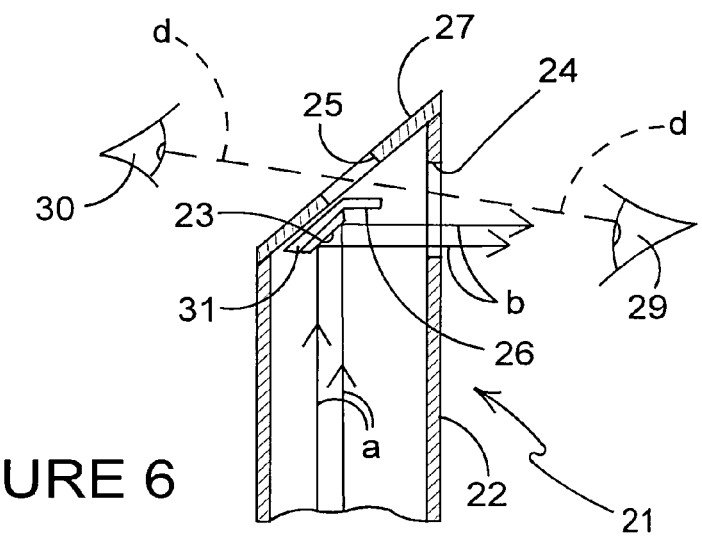
FIG. 6 shows a partial section of a first embodiment of ophthalmoscope in accordance with the invention and in use.

Referring therefore to FIG. 6, a first embodiment of ophthalmoscope, indicated generally at 21, comprises an opaque tube 22 of which only the top end is shown and which defines a first light path a, reflective means in the form of a planar semi-circular mirror 23, a first window 24 formed as a circular aperture in the side wall of the tube 22, a second window 25 in the form of a circular aperture in the roof 27 of the tube 22 and a baffle 26 in the form of a flange located between the first light path a and the second window 25. As can be seen, no lenses are employed.

Light passing along a first light path a from a light source (not shown), such as the light source 8 of a light pen 12 shown in FIG. 2, is reflected through 90° at the 45° angled mirror 23 along a second light path b which then passes through the first window 24 and then into a subject eye 29.

The mirror 23 is mounted to a downwardly extending extension 31 of the flanged baffle 26, at 45° thereto.

The eye 30 of an observing user is able to view the retina of the subject eye 29 along a path d extending through the second and first windows 25, 24, such path d being generally parallel to the second light path b.

Because the baffle 26, and to a certain extent its extension 31, is located between the first light path a and the second viewing window 25, any light which might otherwise pass through that window 25 into the eye 30 of an user, is eliminated or at least substantially reduced, thereby substantially reducing glare and enhancing the user's view of the subject eye 29.

Spurious light which is not diverted along the light path b is substantially absorbed by the matt black interior surface of the tube 22.

Turning now to the second embodiment of ophthalmoscope 41 shown in FIGS. 7 to 9, again only the top end of a tube 42 defining a first light path a is shown, along with a planar mirror 43, a first window 44 in the form of a circular aperture in the side wall of the tube 42, a second window 45 in the form of a circular aperture in the roof 47 of the tube 42 and a block 46 upon which the mirror 43 is mounted and which, in turn, is mounted to the tube roof 47. Again, also, no lenses are used.

Light from a light source passing along the first light path a defined by the tube 42, is reflected by the mirror 43 through 90° along the light path b and then into a subject eye 49.

That eye 49 can be viewed by the eye 50 of an observing user along a path d extending through the second and first windows 45, 44.

The combination of the block 46 and mirror 43, as well as the dimensions thereof, and particularly the thickness, of the block 46, acts as a baffle between the first light path a and second viewing window 45, thereby eliminating, or at least substantially reducing, any glare which might otherwise enter the user's eye via the second viewing window 45 and which is thus prevented from doing so.

Figure 7:
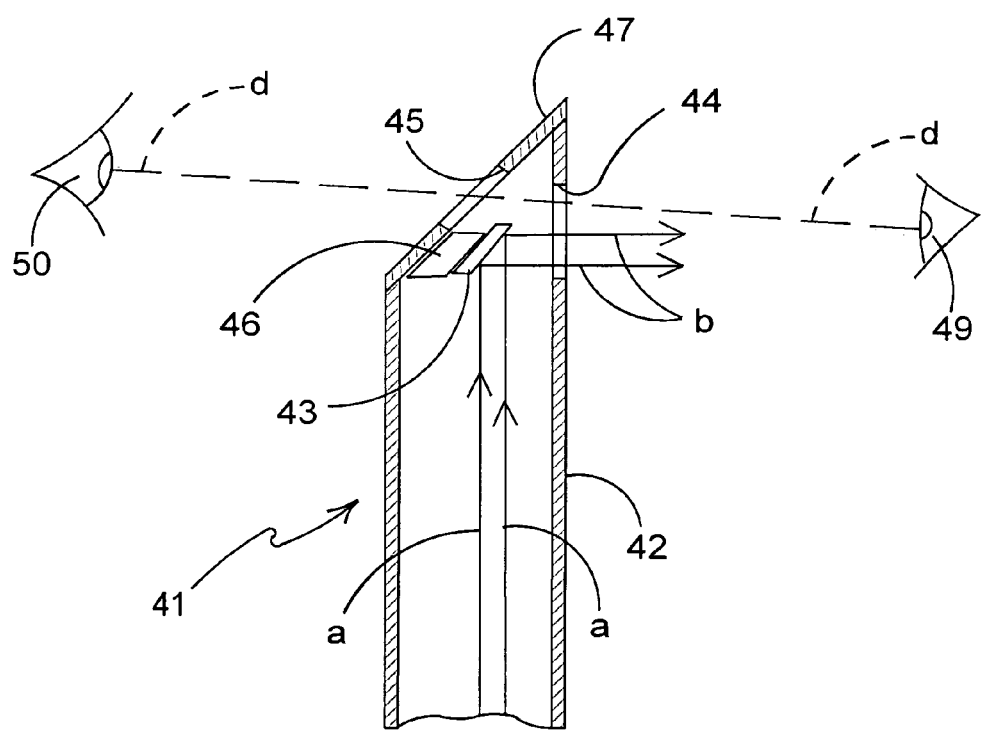
FIGS. 7 to 9 show a second embodiment, again in partial section, of ophthalmoscope in accordance with the invention and in use.
Figure 8:
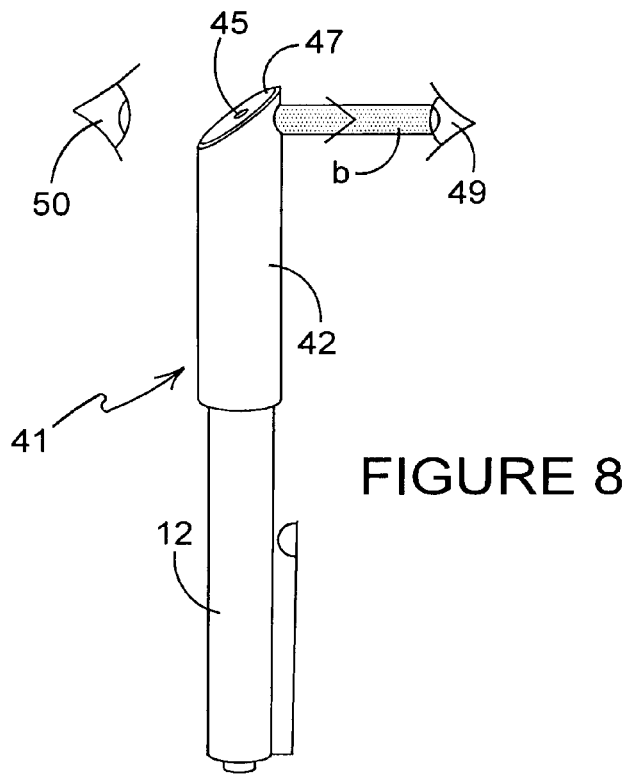
Figure 9:
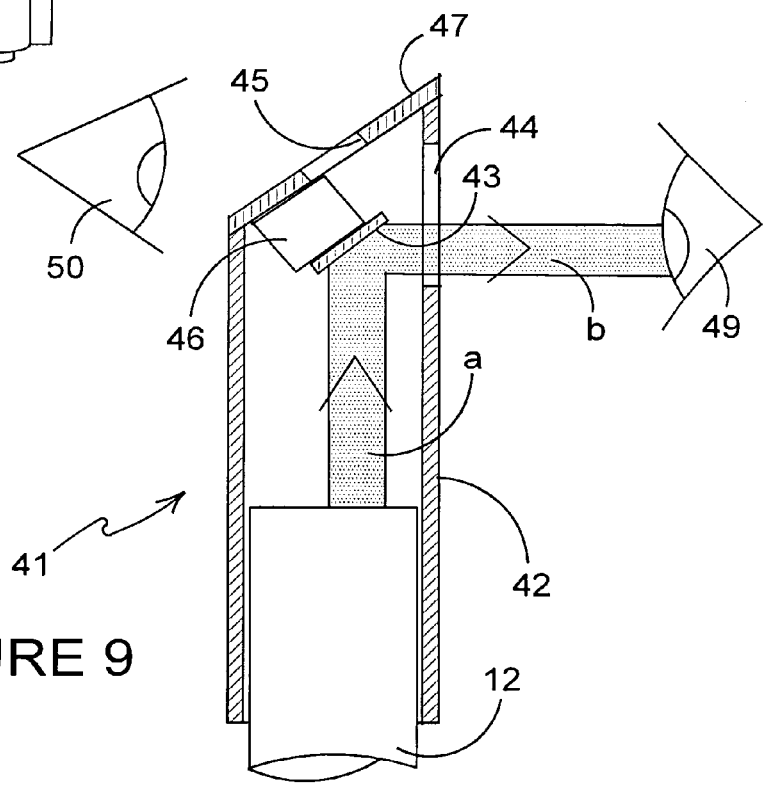

As in the case of the first embodiment described above in relation to FIG. 6, this second embodiment also enhances the viewing capability of a user's eye 50 into the subject eye 49 along the path d, as shown in FIGS. 6 and 7, which is substantially parallel to the second light path b.

It is to be appreciated that the mirror 43 and supporting block 46 of the second embodiment described above in relation to FIGS. 8 and 9 may be replaced by the mirror 23 and flanged baffle 26 of the first embodiment described above in relation to FIG. 6.

Thus, it can be seen that an ophthalmoscope 21, 41 in accordance with the invention eliminates, or at least substantially reduces, any glare in the eye of an observing user, thereby dramatically improving the user's view of a subject eye, whilst also eliminating the use of lenses, thereby reducing manufacturing cost considerably.

The invention claimed is:

1. A lens-free ophthalmoscope comprising:
   means defining a first light path (a);
   reflective means arranged to divert light from the first light path (a) along a second light path (b) extending through a first window and into a subject eye;
   a second window through which an user can view a subject eye along a path (d) extending generally parallel to the second light path (b); and
   a baffle arranged between the first light path (a) and second window to prevent, or at least substantially reduce, any light from the first light path (a) from exiting the ophthalmoscope through the second window;
   wherein said reflective means is mounted on the baffle.

2. A lens-free ophthalmoscope as claimed in claim 1, wherein the first light path (a) defining means comprises a tube.

3. A lens-free ophthalmoscope as claimed in claim 2, wherein at least the outer surface of the tube is opaque.

4. A lens-free ophthalmoscope as claimed in claim 2, wherein the inner surface of the tube is non-reflective.

5. A lens-free ophthalmoscope as claimed in claim 1, wherein said reflective means comprises a mirror.

6. A lens-free ophthalmoscope as claimed in claim 5, wherein the mirror is semi-circular.

7. A lens-free ophthalmoscope as claimed in claim 1, wherein said reflective means is inclined at approximately 45° to the first light path (a) and/or the second light path (b).

8. A lens-free ophthalmoscope as claimed in claim 1, wherein the reflective means comprises a prism.

9. A lens-free ophthalmoscope according to claim 1, wherein the first window is an aperture.

10. A lens-free ophthalmoscope according to claim 1, wherein the second window is an aperture.

11. A lens-free ophthalmoscope according to claim 1, wherein the baffle comprises a flange.

12. A lens-free ophthalmoscope according to claim 1, wherein the baffle comprises a block.

* * * * *